(12) United States Patent
Bansal (10) Patent No.: US 9,566,297 B2
(45) Date of Patent: *Feb. 14, 2017

(54) METHODS AND COMPOSITIONS FOR INHIBITING CELLULAR PROLIFERATION AND SURGICAL ADHESION

(71) Applicant: NovelMed Therapeutics, Inc., Cleveland, OH (US)

(72) Inventor: Rekha Bansal, Cleveland, OH (US)

(73) Assignee: Novelmed Therapeutics, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/223,267

(22) Filed: Mar. 24, 2014

(65) Prior Publication Data

US 2014/0206644 A1    Jul. 24, 2014

Related U.S. Application Data

(63) Continuation-in-part of application No. 13/202,006, filed as application No. PCT/US2010/024452 on Feb. 17, 2010, now Pat. No. 8,680,075.

(60) Provisional application No. 61/152,988, filed on Feb. 17, 2009.

(51) Int. Cl.
| | |
|---|---|
| *A61K 31/737* | (2006.01) |
| *A61K 31/721* | (2006.01) |
| *A61K 31/715* | (2006.01) |
| *C08B 37/02* | (2006.01) |
| *A61K 47/48* | (2006.01) |
| *A61K 31/727* | (2006.01) |
| *A61K 31/728* | (2006.01) |
| *A61K 31/734* | (2006.01) |

(52) U.S. Cl.
CPC ........... *A61K 31/737* (2013.01); *A61K 31/727* (2013.01); *A61K 31/728* (2013.01); *A61K 31/734* (2013.01); *A61K 47/4823* (2013.01)

(58) Field of Classification Search
CPC   A61K 31/737; A61K 31/727; A61K 47/4823; A61K 31/734; A61K 31/728
USPC ........... 514/59, 54, 56, 55.1; 536/123.1, 112
See application file for complete search history.

(56) References Cited

U.S. PATENT DOCUMENTS

| | | | | |
|---|---|---|---|---|
| 6,417,173 | B1 * | 7/2002 | Roufa et al. | 514/54 |
| 6,663,864 | B1 * | 12/2003 | Kink et al. | 424/158.1 |
| 2005/0183731 | A1 * | 8/2005 | Hunter et al. | 128/898 |

FOREIGN PATENT DOCUMENTS

| | | |
|---|---|---|
| CA | 2555036 A1 | 9/2005 |
| CA | 2624867 A1 | 4/2007 |
| CA | 2685208 A1 | 11/2008 |
| CN | 101312747 A | 11/2008 |
| WO | 2007042470 A2 | 4/2007 |
| WO | 2008134430 A1 | 11/2008 |

OTHER PUBLICATIONS

Yvette, B.J. Aldenhoff, et al., "Platelet Adhesion Studies on dupyridamole coated polyurethan surfaces", European Cells & Materials, vol. 5, Jun. 30, 2003, pp. 61-67.

* cited by examiner

*Primary Examiner* — Shaojia Anna Jiang
*Assistant Examiner* — Michael C Henry
(74) *Attorney, Agent, or Firm* — Tarolli, Sundheim, Covell & Tummino LLP (57) ABSTRACT

The present invention provides compositions and methods to inhibit fibrosis and scarring associated with surgery. The present invention relates to the discovery that a synthetic anionic polymer consisting of dextran-sulfate (anionic carbohydrate) conjugated to Tirofiban (an anti-platelet agent which prevents platelet activation and aggregation) can effectively inhibit adhesions that form during surgery. This application is a continuation in part to U.S. patent application Ser. No. 13/202,006. The novel biocompatible conjugate compound of the original application can effectively inhibit fibrosis, scar formation, and surgical adhesions. The invention is predicated on the discovery that the conjugate compound effectively inhibits the invasion of cells which is associated with detrimental healing processes without affecting platelet populations. Use of any of several different anionic components with any of several different anti-platelet agents results in many different specific embodiments of the invention. Thus, the invention provides a large number of materials for use in methods of inhibiting fibrosis and fibroblast invasion. The anionic component for use in the invention includes all proteoglycans, glyosaminoglycans, pentosan polysulfates, alginates and the anti-platelet agent can be on synthetic, peptides, proteins or antibodies. A preferred embodiment of the invention is one in which the conjugate compound dextran sulfate is paired with pentosan polysulfate. In a more preferred specific embodiment, dextran sulfate, in which the sulfur content is greater than about 10% by weight, may be used. In a more preferred embodiment, the average molecular weight of the final bound compound is approximately 40,000 to 500,000 Daltons.

14 Claims, 12 Drawing Sheets

Note: "NM3014 is Dextran Sulfate only

Figure 5: rat uterine horn adhesion model

METHODS AND COMPOSITIONS FOR INHIBITING CELLULAR PROLIFERATION AND SURGICAL ADHESION

RELATED APPLICATION

This application is a Continuation-in-Part of U.S. patent application Ser. No. 13/202,006, filed Aug. 17, 2011, which is a National Phase Filing of PCT/US2010/024452, filed Feb. 17, 2010, which claims priority to U.S. Provisional Application Ser. No. 61/152,988, Feb. 17, 2010. The subject matter of which are incorporated by reference in their entirety.

DESCRIPTION

This application discloses and claims an additional new embodiment of the original invention, which was developed subsequent to the filing of the parent application. The new embodiment is a preferred embodiment wherein the compound is a non-covalently bound salt of an anionic carbohydrate (such as dextran sulfate) and a positively charged anti-platelet (and/or anti-coagulant) compound (such as Tirofiban).

FIELD OF THE INVENTION

The present invention is directed towards a new composition matter, which is a compound used in preventing cellular proliferation and adhesions that form during and after surgery. The compound consists of an anionic monomer, or polymer, which is covalently linked to an anti-platelet agent. The new molecule is then mixed with Gel-Foam to form a device for implantation at the surgical site. The composition can also be used effectively in a scenario in which both anionic monomer/polymer and the anti-platelet agent are present in a formulation without the covalent bond between the anionic compound and the anti-platelet agent. Embodiments of the invention include methods using such compositions to inhibit invasion and proliferation resulting in fibrosis and attendant complications such as scar formation and surgical adhesions. The types of anti-platelet agents which can be used to construct the compound include synthetic anti-platelet compounds, anti-platelet proteins, anti-platelet polypeptides, or antibodies which inhibit platelets. The most preferred embodiment of the invention is a composition which is a carefully constructed salt of dextran-sulfate and Tirofiban.

BACKGROUND OF THE INVENTION

Approximately 1.8 million abdominal surgeries are performed in United States each year. Postoperative adhesions occur in 67-93% of the people who undergo these abdominal surgeries. In the United States, the annual expense of removing abdominal adhesions is estimated to be in excess of 2 billion dollars. Worldwide total surgical procedures are as follows; Lumbar (800,000), Tendon/Nerve (500,000), Abdominal (2 million), Pelvic (2.6 million, Implants (2 million), and cardiac (2 million). All of these surgical procedures can cause the formation of extensive post-operative adhesions. While adhesions are inevitable in several types of surgeries, good surgical technique combined with therapeutic agents, such as the invention claimed in this application, can greatly reduce the likelihood and/or extent of adhesion formation. Detrimental and painful adhesions can also form as a result of non-surgical physical injury. In the case of severe physical injury, adhesions can form at the wound site, during wound healing.

In both the cases of surgery and non-surgical physical injury, organs or tissues attach to each other via scar tissue and introduce clinical problems. While the formation of scar tissue is part of the normal healing process and is required for proper wound healing, in some cases the scar tissue overgrows. When the scar tissue proliferates beyond the boundaries of the wound, this extraneous scar tissue creates adhesions between otherwise healthy tissues. These adhesions are often painful and may lead to other problems. In extreme cases, adhesions can lead to intestinal obstruction, female infertility, organ failure, paralysis and even death. Formation of such adhesions restrict the normal mobility and function of affected body parts and are therefore named as complications of almost all major surgical procedures and is frequently observed after serious physical injury. The compound of this invention is a new composition of matter and can be used in a variety of surgeries, and as part of treatment for non-surgical physical injury, where inhibition of adhesion formation and improved wound healing is required.

The use of Dextran-70, Lactated Ringers, Hyaluronic acid, cellulosic, crosslinked hyaluronic acids, glycosaminoglycans, and synthetic & natural polymers have been used with some success.[1] Additionally, the use of drugs such as tissue plasminogen activator, tolmetin, ibuprofen, dexamethasone, and verapamil in preventing adhesions has also been reported. A few of the clinical applications include use in surgeries of the lumbar region, tendons, peripheral nerves, and surgeries which apply implants. Adhesion reducing compounds and devices can be used to prevent pelvic adhesions, abdominal adhesions, cardiac adhesions, ophthalmic adhesions, and adhesions forming in the sinuses. A number of animal models are available to evaluate the effect of compounds for a particular indication of interest. For example, these models include laminectomy in rats and rabbits, flexor tenolysis in rabbits and chickens, sciatic nerve neurolysis in rats, breast implants in rabbits, steronotomy in rabbits, cardiac procedures in rats and rabbits, and fallopian tube procedures in rats and rabbits. Bowl adhesions can be induced in rats and rabbits. The uterine abrasion model can be used in rats and rabbits. Use of these models for novel compound evaluation has been accepted within the art. In these models, reduction in the development of scar tissue is evidence of a reduction in the formation of adhesions. There exists significant association between scar tissue formation and adhesion formation. It is known within the medical profession that reduction in the formation of adhesions and excessive scar tissue leads to improved surgical outcome, and improved recovery from physical injury.

Large numbers of cases have been reported that deal with the adhesions as a result of surgery. While different types surgical procedures lead to adhesions of various severities and consequences, depending on the extent and location of the procedure, the outcome of any surgical procedure can be improved if adhesions are prevented. Improved surgical outcomes reduce the healthcare costs, and indirect costs, of post-operative recovery. After a patient undergoes back surgery, severe adhesions are often reported. The formation of these adhesions leads to severe back pain and increases the difficulty of repeated surgery. Both, lumbar laminectomy and discectomy surgeries cause recurrent radicular pain.

Dextran Sulfate only has been used in reducing surgical adhesions with limited success in human patients. Dextran sulfate alone does not prevent the accumulation of cellular debris which results from the destruction of platelets.

Destruction of platelets occurs as a consequence of platelet aggregation. Agents which prevent platelet aggregation can thus prevent platelet destruction and the corresponding accumulation of cellular debris from destroyed platelet cells. The new compound, claimed in this invention, was prepared by covalent conjugation of Tirofiban (which prevents the formation of platelet aggregates) to Dextran Sulfate. This new conjugate compound prevents 3T3 cell proliferation, glioma cell proliferation, and platelet break-down. The invention is the first anti-adhesion therapeutic which prevents the formation of excessive scar tissue while also preventing platelet aggregation, platelet destruction, and accumulation of cellular debris resulting from platelet destruction.

A newly developed embodiment of the claimed invention consists of an anionic carbohydrate (such as dextran sulfate) paired with an anti-platelet aggregation compound (such as Tirofiban), in a non-covalently bound salt formation.

SUMMARY OF THE INVENTION

The present invention demonstrates that the conjugate molecules of molecular weight 500 to 500,000, which are anionic in nature and which contain an agent which prevents platelet activation and aggregation, can effectively inhibit excessive scar formation. In particular, these compounds can prevent the scar tissue which forms surgical adhesions. These compounds inhibit cell invasion and peridural fibrosis. Such compounds are useful in inhibiting fibroblast invasion, thus regulating both the wound-healing process and preventing fibrosis. These conjugate compounds inhibit cell proliferation, cell invasion, monocyte and neutrophil cell infiltration into the surgical site.

The anionic moiety of the conjugate includes dextran sulfate, pentosan polysulfate in addition to glycosaminoglycans such as dermatan sulfate, chondroitin sulfate, keratan sulfate, heparan sulfate, heparin, and alginate. Because these molecules can inhibit fibroblast proliferation, invasion or migration in the presence of conjugate compounds. While dextran sulfate and molecules and compositions comprising dextran sulfate are desired.

The invention is further directed to methods of using an inhibitory anionic conjugate, preferably with the dextran sulfate moiety combined with Tirofiban to inhibit fibroblast invasion and fibrosis, and also to inhibit cellular invasion and promotes wound healing as a result of platelet preservation. The invention therefore provides methods to inhibit fibroblast invasion, glial invasion, and promote wound healing. Having both Dextran Sulfate and Tirofiban allows prevention of scar formation.

In a preferred embodiment, the platelet preservation agent is attached to the dextran sulfate molecule, which gives it a unique composition where the moiety provides both inhibition of scar formation and promotion of wound healing. In another embodiment, molecules comprising one of the inhibitory conjugate compounds may be used with one or more other inhibitory conjugate compounds, and an anti-platelet agent.

The instant invention further provides compositions comprising inhibitory anionic compound conjugate and a suitable molecule conjugate, and methods to administer the compositions to inhibit scar formation via the inhibition of invasion of glial cells. The present invention also provides compositions comprising effective amounts of an inhibitory conjugate compound conjugate, preferably dextran sulfate-aggrastat conjugate an effective amount of an adhesive protein, and a pharmaceutically acceptable carrier.

The most currently developed preferred embodiment of the invention is one in which dextran sulfate (with a negative charge density) is non-covalently bound to Tirofiban in a salt formation. Tirofiban has very low solubility in water. It has a higher solubility in methanol. Dissolution of Tiroban in methnol, followed by titration into dextran sulfate, will result in the formation of a water-soluble compound which contains both the anionic carbohydrate and the anti-platelet compound bound in a non-covalent bond. Formation of this salt allows for the compound to be dissolved in water.

DETAILED DESCRIPTION OF THE INVENTION

The present invention relates to the discovery that certain biocompatible conjugate compounds can effectively inhibit scar formation, in particular surgical adhesions, when these anionic compounds, are conjugated with an anti-platelet agents. Such conjugates prevent fibrosis and infiltration of neutrophils and monocytes at the site. The conjugate compound effectively inhibits invasion of cells associated with detrimental healing processes, i.e., fibrosis, and scarring. The conjugate compound of the present invention are useful to inhibit fibroblast invasion, thus regulating the healing process and preventing fibrosis. The conjugate compounds of the present invention inhibit glial-cell invasion, neutrophil and monocyte/macrophage invasion. The conjugate compound in combination with the anti-platelet agent aggrastat, inhibits glial cell invasion, 3T3 cell invasion, neutrophil and monocyte invasion. Thus the present invention teaches a large number of materials for use in inhibition of scar formation, fibrosis, and surgical adhesions.

Inhibitory conjugate compound moiety of "the conjugate-compound" for use in the invention include dextran sulfate (DX) and pentosan polysulfate (PS), dermatan sulfate (DS), chondroitin sulfate (CS), keratan sulfate (KS), heparan sulfate (HS), Fragmin, and heparin (HN) may be used. At suitable concentrations, the foregoing molecules can inhibit fibroblast invasion or migration. In the preferred embodiment, the present invention is directed to methods of using DX, and molecules and compositions comprising DX, to inhibit, prevent or regulate fibroblast invasion and fibrosis and therapeutically, where the foregoing is desired.

The instant invention further provides pharmaceutical compositions comprising inhibitory conjugate compounds or inhibitory conjugate compounds and an anti-platelet moiety, in a pharmaceutically acceptable carrier, and-methods to administer the compositions to inhibit scar formation, and fibrosis to inhibit undesired invasion of glial cells, fibroblasts, and neurite outgrowth.

The compositions and methods of the present invention are suitable for treatment of animals, preferably mammals, and more preferably humans. A therapeutically effective amount of a composition comprising a conjugate compound of the invention can be administered to a lesion in an animal for any of the methods disclosed.

Compositions to Prevent Fibrosis and Cell Invasion:

The invention provides compositions for use in inhibiting fibroblast invasion, glial cell invasion, neurite outgrowth, neutrophil invasion, neutrophil and monocyte/macrophage invasion. In particular the compositions are useful in preventing fibrosis and scar formation, e.g., surgical adhesions. The compositions comprise inhibitory conjugate compounds of the invention. The conjugate compound should preferably be present at a concentration greater than about 1 mg/ml, more preferably in the range of 20-200 mg/ml. In a preferred embodiment, the conjugate compound is dextran sulfate and the anti-platelet agent should be aggrastat. In a more preferred embodiment, the conjugate compound is dextran sulfate, in which the sulfur content is greater than about 10% by weight.

The mixture of "the conjugate compound" with the saline and gelfoam may yield a viscous liquid or gel. Any component or a compound that may cause gel formation is incorporated as a skilled art. The biocompatible anionic conjugate compound of the invention may be combined with a solid or semi-solid excipient or carrier, such as paste, gel, foam or sheet. The conjugate compound of the invention may be mixed with said carrier or excipient in a colloidal suspension or admixture; alternatively, the carrier or excipient may be impregnated with the conjugate compound to form the composition. Preferred semi-solid carriers include dextran gels, such as HYSKON-70 (Pharmacia), INTERCEED (Johnson & Johnson), native collagen gels, and denatured collagen gels, such as GELFOAM (Upjohn).

General Indications: The inhibitory compositions comprising an inhibitory The compound conjugate can be used as barriers to cell migration or invasion caused by trauma, surgery, infection (viral or bacterial), metabolic disease, malignancy, exposure to toxic agents, and other hyperplastic situations. Coating an organ or tissue with an inhibitory composition may be preventive or prophylactic. Inhibitory-adhesive compositions provide a preferred coating composition.

Surgery: In one embodiment, epidural (or peridural) fibrosis may be inhibited by application of a composition of the instant invention to the surgical lesion. The conjugate compound can be in solution, bound to substrate, trapped in a carrier protein or polymer. In one embodiment, the conjugate compound may be applied in a carrier or excipient such as a paste, gel, or sheet.

In yet another embodiment, the present invention provides a composition and method to inhibit fibrosis and scarring of fallopian tissue. In particular, fibrosis and scarring of lesions in and around the fallopian tube subsequent to surgery can be inhibited. Fibrosis of fallopian tubes, resulting from infection or other causes, is a cause of infertility in 25-30% of the cases. Pelvic sidewall adhesions are also implicated in infertility. Since scar tissue forms subsequent to surgery, surgical removal of adhesions alone is not adequate treatment. Thus the present invention has an important application in management of infertility. Other surgical indications include but are not limited to abdominal surgery, joint surgery, tendon surgery, surgery to remove pelvic sidewall adhesions, peritoneal surgery, thoracic surgery, vascular surgery, and cardiac surgery, in particular bypass surgery, valve replacement surgery, cardiovascular surgery, or other open heart surgery.

In another embodiment, the conjugate compounds of the invention may be used in a method of inhibiting fibrosis around an implant comprising applying a composition containing therapeutically effective amount of the conjugate compound. Examples of implants where inhibition of scar formation and fibrosis is desired include, but are not limited to, nephrostomy tube, peritoneal drainage tube, artificial hip joint, artificial heart valve, peripheral nerve repair and other prostheses and intravenous catheter. Implants may be treated by coating or impregnating with a composition provided by the invention.

Treatment of Fibrotic Lesions in Joints: Joint lesions are corrected using surgical procedures which can cause adhesions. These processes have the disadvantage of inducing further fibrosis during the healing process. Administration of a composition comprising an inhibitory conjugate compound of the present invention would inhibit subsequent fibrosis and adhesion formation in the joint, thus increasing the chance of successful therapy.

Modes of Administration: Methods of introduction of the inhibitory conjugate compound or the inhibitory-adhesive compositions of the invention are well known in the art. The new compound conjugate of the present invention will be mixed with the collagen gels using methods well known in the art to make an implantable device for prevention of adhesion that form following surgery. Such compositions of the invention will be placed into and around the site of interest by any suitable route. This may be achieved by, for example, but not by way of limitation, local infusion or application during surgery, by injection, by aerosol, by means of a catheter, or by means of an implant, said implant being of porous, non-porous, or gelatinous material, including membranes, such as silastic membranes, or fibers. In a preferred embodiment, the implant is coated or impregnated with an inhibitory-adhesive composition of this invention. Polymer implants treated with inhibitory molecule or, more preferably, coated with inhibitory-adhesive, can be applied or inserted at the desired site of treatment. Such polymers can have various compositions, pore sizes, and geometries. Polymers that can be used include but are not limited to those made of nitrocellulose, polyanhydrides, and acrylic polymers.

The invention provides for application of an inhibitory composition or inhibitory-adhesive composition by surgical procedures. The inhibitory conjugate compound or inhibitory-adhesive may be applied-to a surgical wound. The conjugate compound or inhibitory-adhesive may be directly applied to sites of tissue injury, or to coat an entire organ or to close a surgical incision. Where suitable, administration of the inhibitory conjugate compound or inhibitory-adhesive composition may be made by orthroscopic procedures.

Scar formation and fibrosis result from uncontrolled invasion of fibroblasts to the site of an injury or lesion. Other detrimental conditions also result from uncontrolled cellular invasion of fibroblasts, neutrophils, and monocytes. Inhibition of fibroblast invasion would prevent scarring and associated surgical adhesions, e.g., peridural fibrosis, and cosmetically inappropriate scars, e.g., following cosmetic or reconstructive surgery. The present invention is about a new compound conjugate which has an anionic component and an anti-platelet components such that the conjugate-compound inhibits adhesion formation in variety of cells.

The most currently developed preferred embodiment of the invention is one in which dextran sulfate (with a negative charge density) is non-covalently bound to Tirofiban in a salt formation. Tirofiban has very low solubility in water. It has a far higher solubility in methanol. Dissolution of Tiroban in methonal, followed by titration into dextran sulfate, will result in the formation of a water-soluble compound which contains both the anionic carbohydrate and the anti-platelet compound bound in a non-covalent bond. Formation of this salt allows for the compound to be dissolved in water.

The salt form of the compound is expected to be compatible with multiple types of application. Two formulations of the salt form of the invention were prepared in 6% Gelfoam and 8% Gelfoam. A formulation of the new compound might also be incorporated into a gel or cream, or other topical formulation, which might be administered to a wound or surgical site and/or the affected areas and organs. The salt form of the compound might also be administered in the form of a spray, or as part of an implantable device.

EXAMPLES

Example-1

NM2040 Inhibits 3T3 Proliferation

Approximately 50,000 cells were plated in a 96 well ELISA plate. The cells were allowed to grow in DMEM with 10% FCS media for 5 days, following which the cells were treated with Cy Quant assay and the inhibition of cellular proliferation was measured using the decreased fluorescence intensity. To evaluate the effect of various concentrations of NM2040 in the cellular proliferation assay, cultures were treated with concentrations ranging from 1 to 600 μg/ml. The total fluorescence intensity was plotted against the concentrations.

Example-2

NM2040 Inhibits Glioma Proliferation

Figure 1:
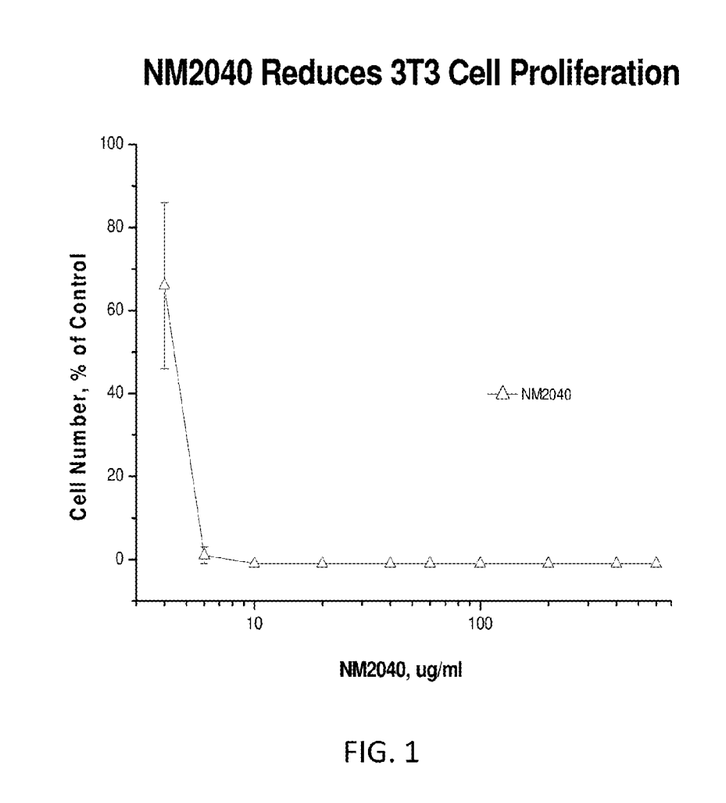
FIG. 1 illustrates NM2040 Inhibits 3T3 Cell Proliferation.
Figure 2:
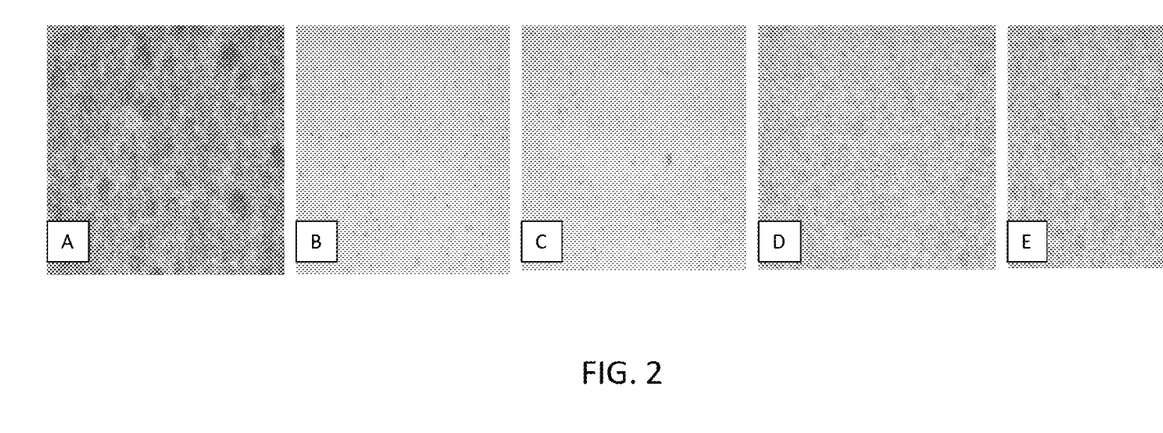
FIG. 2 illustrates NM2040 Inhibits Glioma Proliferation.

This experiment was conducted to demonstrate if NM2040 would inhibit cellular proliferation. In a six well plate, a cloning ring of 6 mm diameter was placed and 60 ul aliquot of cellular suspension (stock containing 320,000 cells/ml of C6 cells) was prepared and placed in the center of each well of a six well plate in the cloning ring. After 4 h, the media was removed and the cells were incubated with Opti-MEM 1× media with and without the compound. These cultures were incubated at 37° C. and with 10% CO2 for five days, following which the pictures were taken as shown in FIG. 2.The compound effect appears to be dose dependent with maximal effect shown at 3 ug/ml. The first panel is for controls (untreated), the second panel at 3 mg/ml, the third panel at 1.5 mg/ml, the fourth panel at 0.75 mg/ml, and the fifth panel at 0.36 mg/ml. The compound NM2040 appears to be inhibitory at all doses with maximal effect seen at nearly 1 mg/ml concentration.

Example-3

Inhibition of C3a and C5a Formation by NM2040

Figure 3:
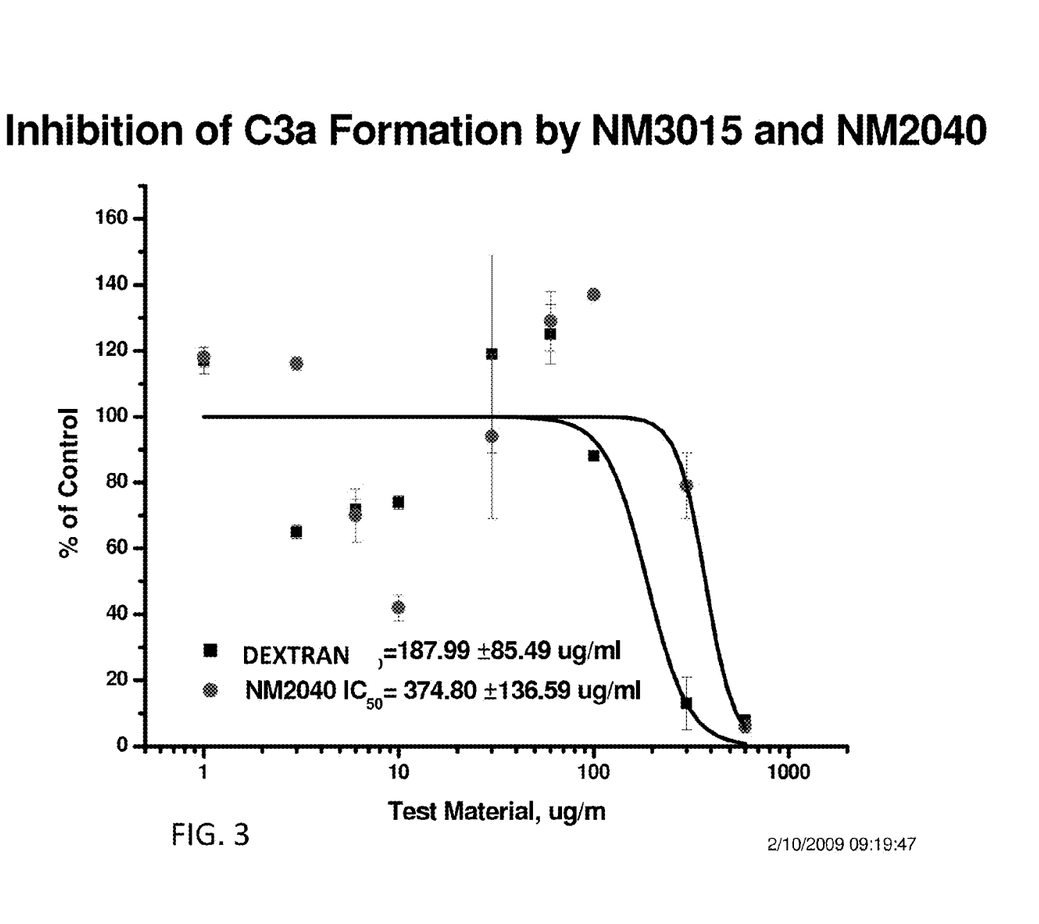
FIGS. 3 & 4 illustrate NM2040 Inhibits C3a and C5a Formation.
Figure 4:
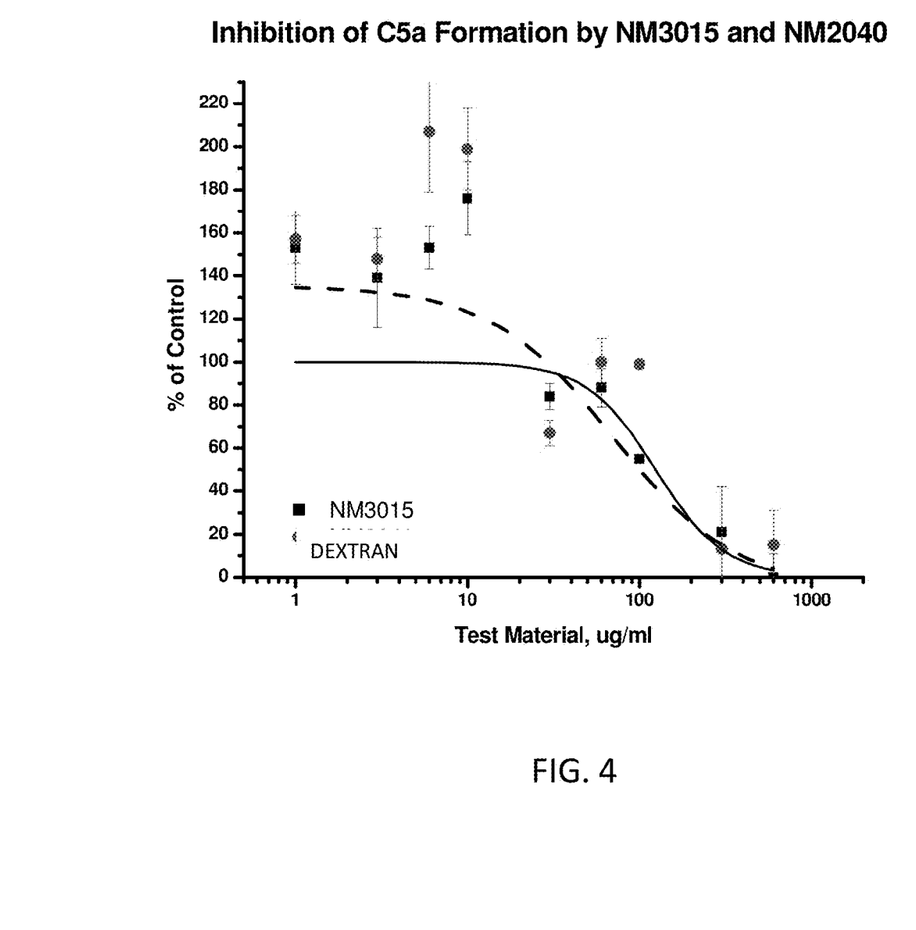
Figure 5:
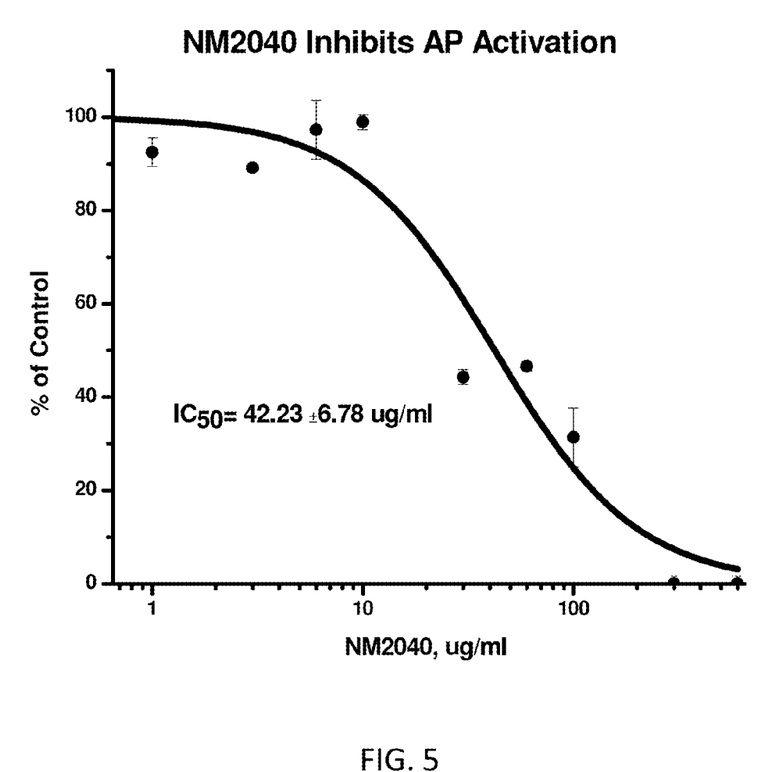
FIG. 5 illustrates NM2040 Inhibits AP activation.
Figures 5, 11:
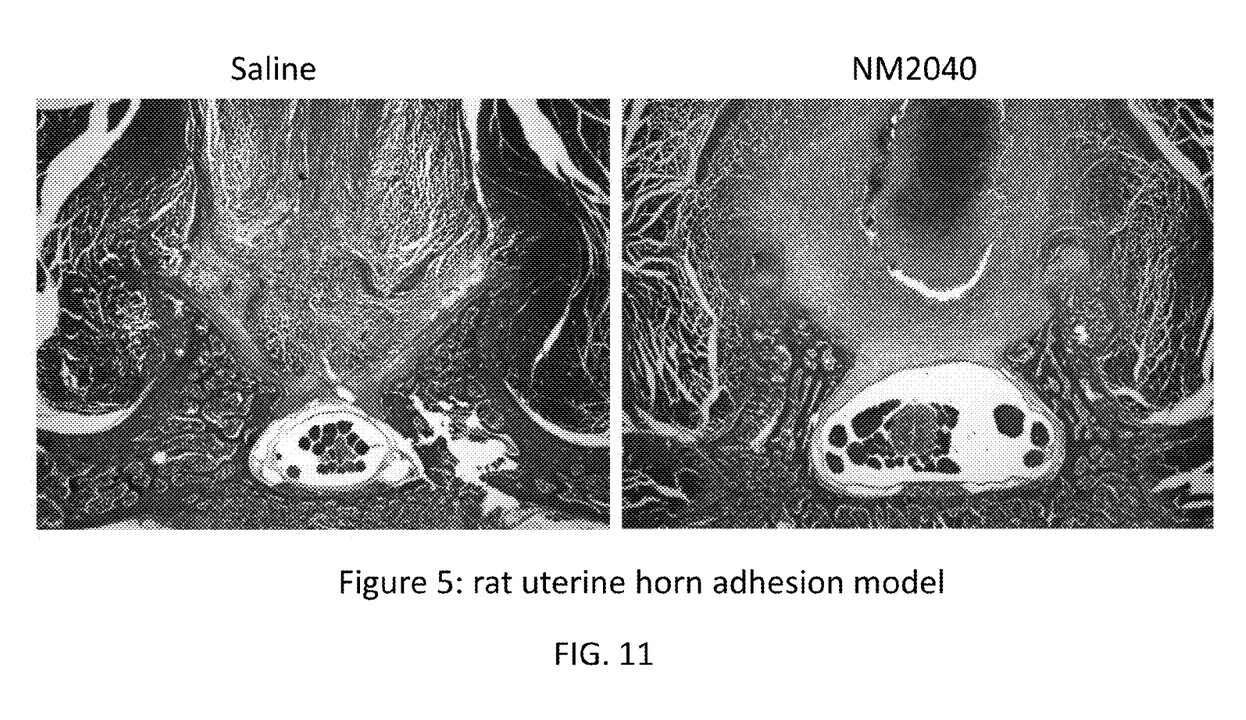
FIG. 11 illustrates NM2040 Improved surgical outcome in subjects treated with NM2040.

Chemotactic peptides are produced at the injury site which can attract inflammatory cells at the injury site causing inflammation. NM2040 was tested to determine if this compound would inhibit the production of the C3a and C5a. The compound was incubated with blood at 37 degree in a rotating tubing loops. Whole blood from a healthy donor was collected into a polypropylene tube containing 5 units of heparin per ml of whole blood. The whole blood was diluted 1:1 with plasmalyte and aliquoted in 2 ml aliquots with and without drug treatments. PVC tubings of 4 mm diameter were filled with 2.0 ml of the heparinized human blood and closed into a loop with a short piece of silicon tubing. Sample and control tubing loops were rotated vertically in a water bath for 2 hours at 37° C. After incubation, blood samples were transferred into 5 ml siliconized eppendorf tubes. The samples were separated into two aliquots; one aliquot was subjected to flow cytometry studies and the other aliquot was centrifuged to separate the plasma for the measurement of C3a and C5a. The plasma samples were diluted to 5% with sample diluent buffer and the amounts of C3a and C5a were determined using ELISA assay kits following the manufacturer's instructions (Quidel Corporation, San Diego Calif.). As shown in FIG. 3, and FIG. 4 NM2040 is able to prevent C3a and C5a production in a dose dependent manner. Both C3a and C5a are chemotactic peptides that are responsible for chemotaxis of neutrophils and monocytes. As shown in FIG. 5, NM2040 inhibits activation of the alternative pathway. In the same experiment NM3015 was also evaluated. This compound is a mixture of Dextran sulfate and Tirofiban.

Example-4

Inhibition of Platelet Damage by NM2040

Figure 6:
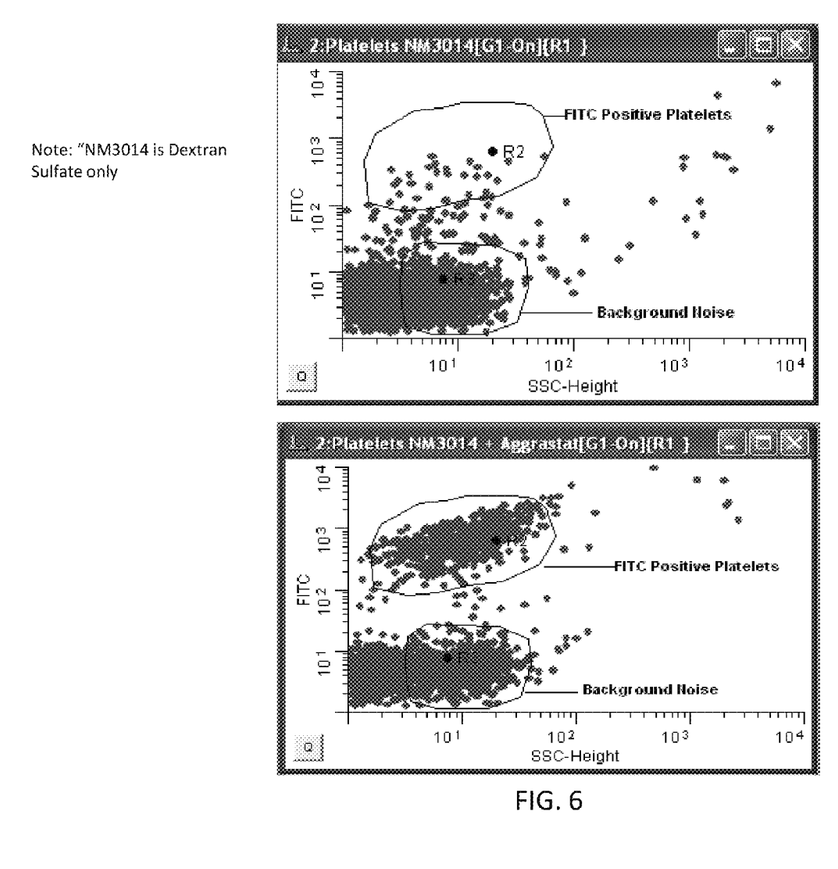
FIG. 6 illustrates NM2040 Inhibits does not affect Platelet Number.
Figure 7:
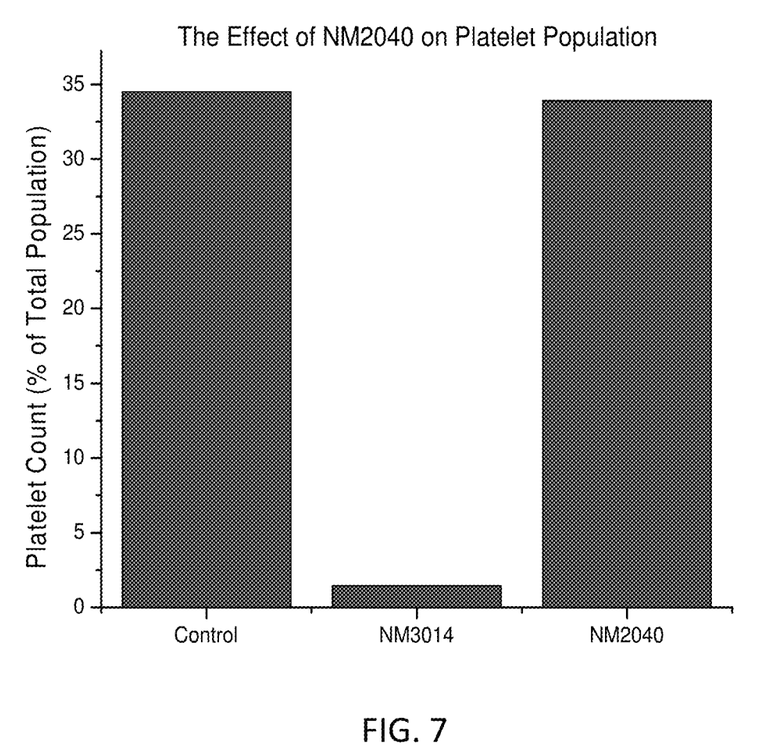
FIG. 7 illustrates Inhibition of Platelet Damage by NM2040.

Aliquots of blood following the tubing loop were stained with fluorescent labeled antibodies for flow cytometry studies. Platelets were stained with FITC labeled CD61 and PE labeled CD62P. In a typical method, 20 ul of each of the labeled antibodies were added to the 100 ul of staining buffer containing 50 ul of whole blood. After 20 minutes, 2.0 ml of staining solution was added and the red blood cells were allowed to lyse for 20 minutes. The solution was centrifuged and the cell pellet was washed with PBS and suspended in 0.5 ml of para-formaldehyde solution. The samples were subjected to flow cytometry using CellQuest, BD-LSR I and the data were analyzed using WinList 5.0. Ln Median was used for calculating the shift in CD11b staining for neutrophils and monocytes. Total numbers of platelets were examined. As shown in FIG. 6 (lower panel) & FIG. 7, NM2040 does not affect the platelets. FITC positive platelets are those platelets that are not damaged and fall in the zone of normal platelets. In contrary, dextran sulfate, by itself, causes greater than 95% loss of total platelets.

Example-5

Inhibition of Neutrophil, Monocyte and Platelet Activation by NM2040

Figure 8:
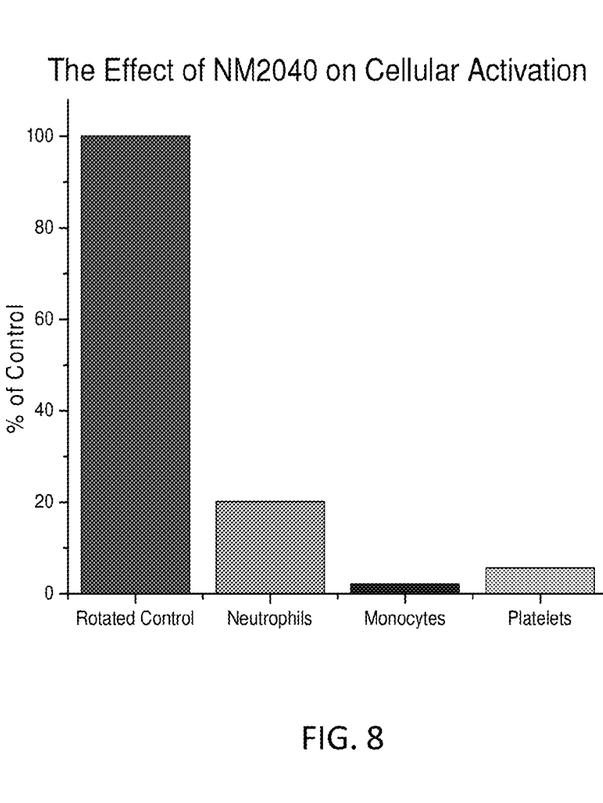
FIG. 8 illustrates NM2040 Inhibits Neutrophil, Monocyte and Platelet Activation.

Aliquots of blood following the tubing loop were stained with fluorescent labeled antibodies for flow cytometry studies. For Example; neutrophils were labeled with FITC labeled CD15 and PE labeled CD11b antibodies, monocytes were stained with FITC labeled CD14 and PE labeled CD11b antibodies, and platelets were stained with FITC labeled CD61 and PE labeled CD62P. In a typical method, 20 ul of each of the labeled antibodies were added to the 100 ul of staining buffer containing 50 ul of whole blood. After 20 minutes, 2.0 ml of staining solution was added and the red blood cells were allowed to lyse for 20 minutes. The solution was centrifuged and the cell pellet was washed with PBS and suspended in 0.5 ml of paraformaldehyde solution. The samples were subjected to flow cytometry using Cell-Quest, BD-LSR I and the data were analyzed using WinList 5.0. Ln Median was used for calculating the shift in CD11b staining for neutrophils and monocytes. % gated dual labeled cells were quantified for platelet populations. As shown in FIG. 8, all three cell types demonstrated significant inhibition of cellular activation.

Example-6

NM2040 Inhibits Adhesions of Spinal Cord to Surrounding Tissue (Epidural Fibrosis) in a Rat Laminectomy The scar tissue attachment to the spinal cord is believed to be the cause of long-term, recurrent pain following laminectomy procedures. The epidural fibrosis refers to the scar tissue that forms following a laminectomy procedure. Laminectomy refers to back surgery of the lamina. Scar tissue forms within the laminectomy site and binds the undersurface of the erector spinae muscles to the posterior and lateral surfaces of the dura mater and to the nerve roots exiting through the dura matter. Epidural fibrosis was investigated after lumbar laminectomy in rats. In this model, a laminectomy is performed at the lumbar 3 (L3) and 5 (L5) vertebrae and then the test agent is applied to the laminectomy site. Subsequently, the laminectomy sites are examined for fibrosis by gross dissection.

Figure 9:
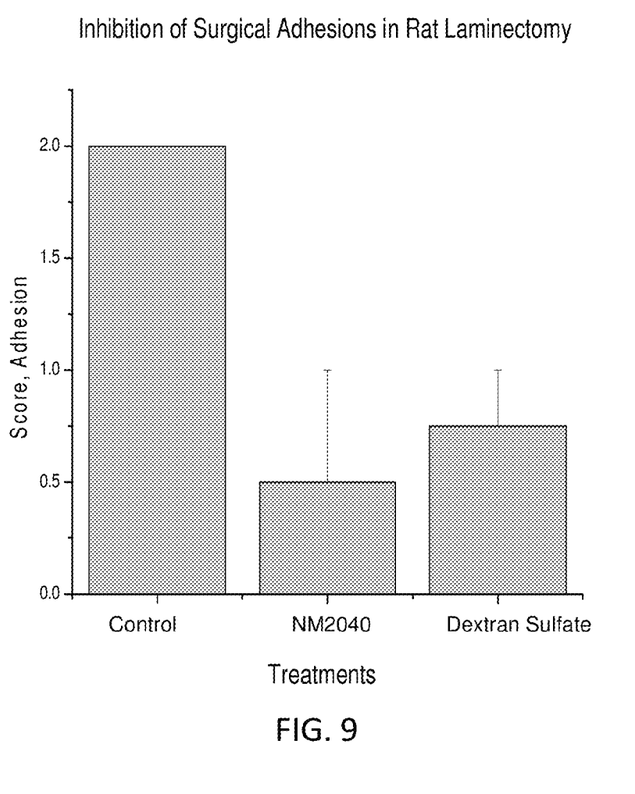
FIG. 9 illustrates NM2040 vs Dextran Sulfate in Inhibition of Surgical Adhesions Following Rat Laminectomy Surgery.

Laminectomies were performed at lumbar vertebrae L3 and L5 to provide auto-controls within each animal. Gelfoam-NM2040 mix was prepared and used on Laminectomy sites in rats. Lewis inbred rats were anesthetized isofluorane. The dorsal skin was incised and the paraspinal muscles were separated from the spinous processes of lumbar vertebrae L2 through L6 to expose the L3 and L5. The spinous processes of L3 and L5 were removed and the vertebral lamina was also removed creating a rectangular laminectomy defect. The test material was placed onto the laminectomy site. The overlying paraspinal muscles were closed over the site by suturing the superficial fascia together and the skin incision was closed with wound clips. After two weeks, animals were subjected to gross evaluation. Rats were anesthetized with anestheticized with isofluorane and the surgical site was reopened by incising the skin and separating the paraspinal muscles. The site, and the tissue was scored 0 to 2. 0 being the "no adhesions", 1 being the lose adhesions, and 2 being the tenacious adhesions. Following the evaluations, rats were euthanized by anesthetic overdose. In all animals, the skin incision and the underlying fascia and paraspinal muscles had healed well. At all laminectomy sites, separation of the paraspinal muscles revealed a layer of scar tissue. Sites treated with the test material demonstrated poor or no adhesion at all and majority of the scores in the group were either zero or 0.5 out of a total of two. The laminectomy site itself had not changed appreciably in size; the borders of the site appeared smooth. The saline treated site served as a negative control. As the scar tissue was removed, bleeding began in and around the site and the site had decreased in size due to adhesion tissue formation. Implantation of NM2040 into the laminectomy site resulted in scores that were significantly lower than implantation of saline controls. These results demonstrate that NM2040 is a potent agent for reducing epidural fibrosis in the rat laminectomy model. The formulation of NM2040 consisted of 10% gelfoan powder, 20 mg/ml final NM2040 in saline. The rat epidural fibrosis model clearly shows that the presence of NM2040 provides a substantial therapeutic benefit by inhibiting fibrosis. As shown in FIG. 9, NM2040 inhibits Surgical adhesions in rat Laminectomy model.

Example-7

Synthesis of NM2040

Figure 10:
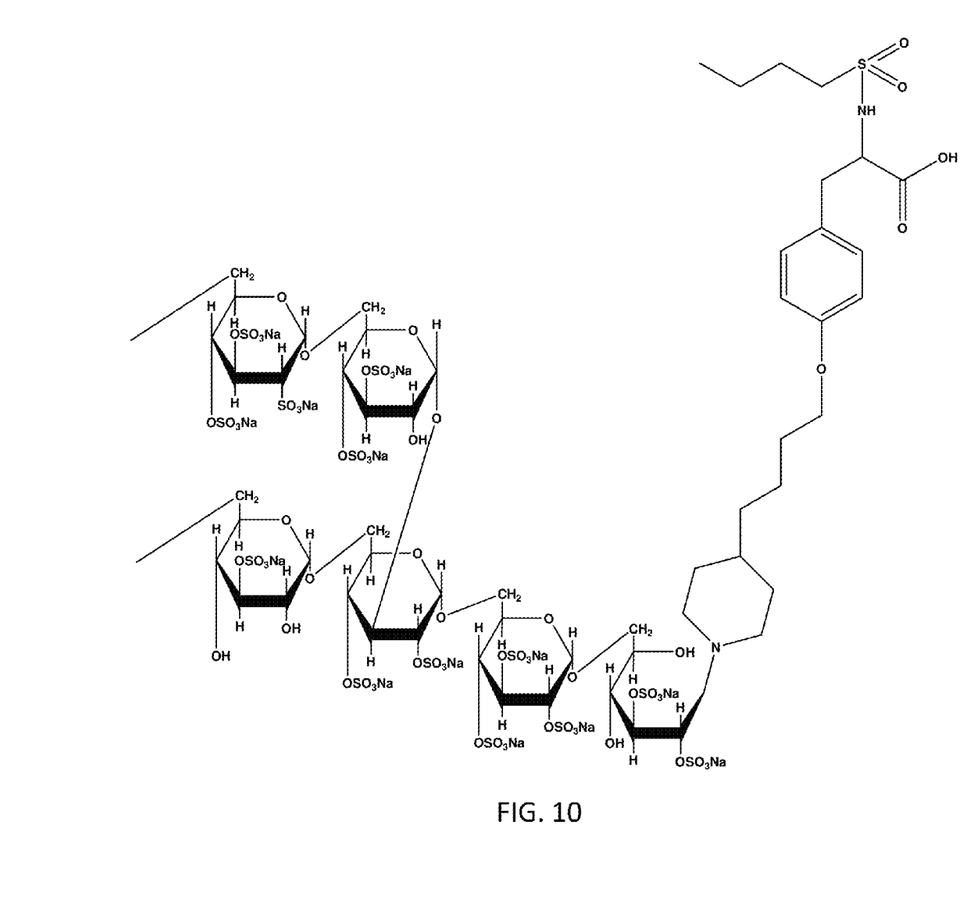
FIG. 10 illustrates NM2040 Synthesis and Structure.

Dextran sulfate has been used for prevention of surgical adhesions. This material activates platelets. The compound presented in this application is a conjugate of the dextran sulfate and Tirofiban which has the platelet preserving function. This combination is called "The Conjugate Compound" as shown in FIG. 10. The compound is prepared as follows; In a 25 mL 2-neck round bottom glass flask, add 1.0 g of dextran sulfate, 2.0 mL water and 10 μL of glacial acetic acid. The contents were stirred overnight at room temperature. The final mixture appeared to be a clear solution. In a separate 10 mL 1-neck flask, add 13 mg of Tirofiban, 1 mL of methanol:water (1:1) mixture, and 10 μL of DMSO. The contents were mixed at room temperature. The final mixture appeared to be a clear solution. Solution from step 2 was added to solution from step 1 and stirred for 2.5-h. Add 315 mg of sodium cyanoborohydride in parts over a period of 15 mins and allow the reaction to proceed for 48 h while monitoring on HPLC. The final solution appeared to be clear. The purification of conjugate was achieved by first filtering through a membrane filter and then through a size-exclusion column. At the end of 48 h, the solution mixture was transferred onto a filter (MWCO 3000, MICRON YM-3) in 500 μL batches and centrifuged at 4000 rpm (1431 gs/RCF) to reduce the total volume to 250 μL. Molecules with smaller molecular size like the sodium cyanoborohydride and excess Tirofiban would pass through the filter, whereas the conjugated product of dextran sulfate-Tirofiban would remain unfiltered. Fresh 250 μL of high purity water was added and the centrifugation procedure repeated to remove small molecular weight contaminants. The process was repeated 4 more times to ensure complete absence of contaminants. The final volume of 250 μL was transferred to eppendorf tubes, frozen at −80° C. and lyophilized for 24 h to get a white solid material. The sample was weighted and re-dissolved in minimum amount of high purity water for further purification using size-exclusion column chromatography. A slurry of Sephadex G-10 in water was poured into a glass column (2.5×75 cm) with the packing height of 36 cm. High purity water was used as the mobile phase at the flow rate of 0.5 mL/min. Void volume of the column was ~720 mL. Fractions of 5 mL were collected every 10 mins using an automated fraction collector (Foxy 200). Each fraction was monitored using UV-VIS spectrophotometer. Fractions 4-9 were pooled based on the similarity of UV profile for Tirofiban. The 30 mL pooled volume was then transferred to a plastic tube, frozen at −80° C. and lyophilized to yield a white powder.

The molar proportions of constituents in the conjugate were obtained using the UV-Vis spectrophotometry. A standard curve was generated for pure Tirofiban. Various concentrations of Tirofiban solution in water were read at $\lambda_{max}$ 275 nm in a UV-Vis spectrophotometer. The following table shows the absorbance readings. Then the absorbance of the conjugate was measured. For a solution of 8.333 mg/mL conjugate concentration, the $A_{275}$ was found to be 0.34 AU. This corresponds to a molar proportion of 1:1.2 for dextran sulfate—Tirofiban conjugate. Both Tirofiban and dextran sulfate-Tirofiban conjugate were subjected to a reverse phase C18 HPLC column to determine if the presence of dextran sulfate in the conjugate would cause a shift in the peak position of Tirofiban. Tirofiban was monitored at 280 nm filters in C18-HPLC. Because dextran sulfate by itself does not carry any aromatic groups, it does not show much absorption at 280 nm. A 20 uL aliquot of the Tirofiban and the conjugate was injected into the column. A methanol: water (1:1) mixture with a flow rate of 0.75 mL/min was used as an eluent. The dextran sulfate—Tirofiban conjugate and the unconjugated Tirofiban profiles were as shown in the figure. The conjugate elutes earlier than unconjugated Tirofiban because of its significantly higher polarity. The sample was prepared by dissolving the conjugate in 0.5 mL deuterated water (D$_2$O). NMR was recorded on INOVA-400 MHz instrument at ambient temperature. The isolated yield of the final conjugate was >95%. This conjugate has the following structure based on its NMR data. The NMR shows the presence of dextran sulfate peaks in the region 3.5-5.5 ppm corresponding to the saccharide protons, while aromatic protons of Tirofiban are seen at 7.0 and 7.2 ppm. The alkyl protons of Tirofiban are seen between 1 and 2 ppm. The chemical name of dextran sulfate-Tirofiban conjugate can be written as the conjugate of dextran sulfate and 2-(butane-1-sulfonylamino)-3-[4-(4-piperidin-4-yl-butoxy)-phenyl]-propionic acid. In this structure the secondary amine of Tirofiban is bonded to the C-1 carbon of the saccharide monomer at the reducing end of dextran sulfate.

Example 9

Development of Dextran-Sulphate and Tiroban Salt

Figure 12:
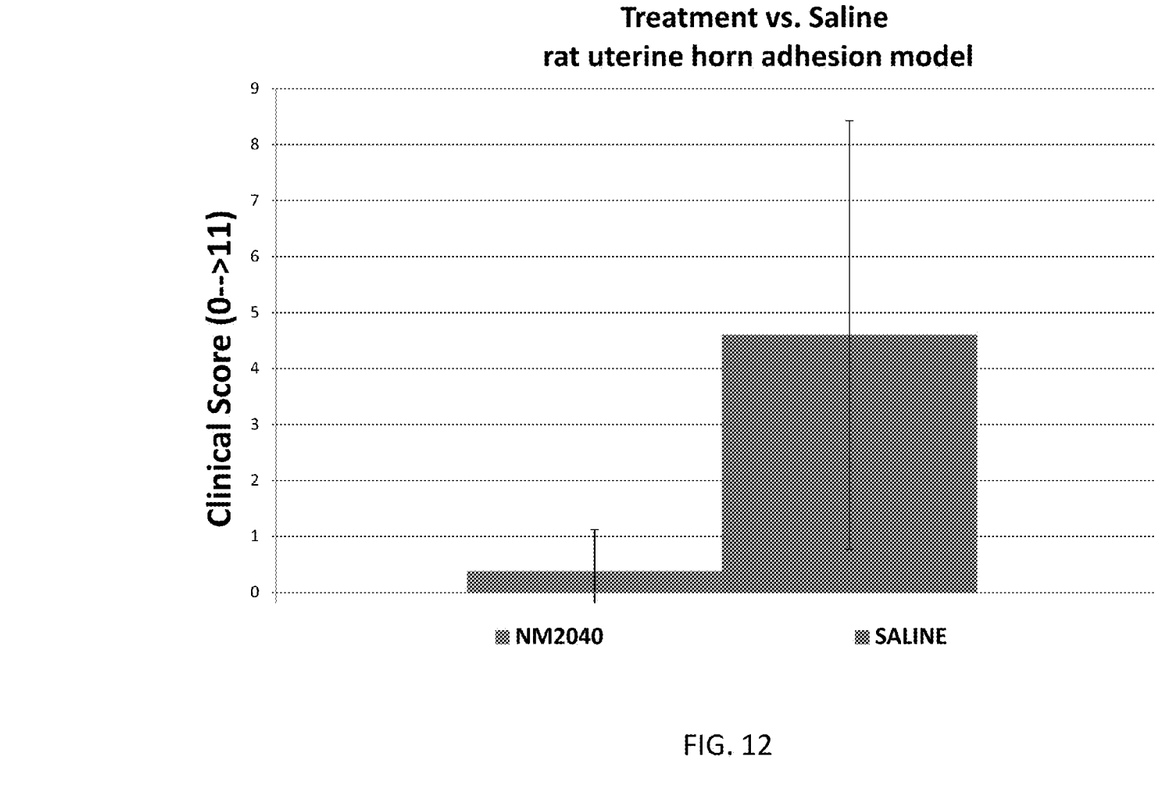
FIG. 12 illustrates Clinical Scores, demonstrating the effectiveness of NM2040.

Dextran Sulfate was combined with an anionic complex using Tirofiban as an anti-platelet compound. A 20 mg/ml solution of dextran sulfate as dissolved in PBS. A 1:50 molar equivalence ratio of Tirofiban:Dextran Sulfate was made for the study. Tirofiban was dissolved in methanol prior to addition. The addition of Tirofiban solution into the Dextran Sulfate solution, via skillful titration, yields the ionic salt. Two formulations were prepared in 6% Gelfoam and 8% Gelfoam. The preparation was used in a rat uterine horn adhesion model. Bipolar caughtery model was used. Adhesion, adhesion characteristics and degree of adhesion were graded. As shown in FIG. 12, the clinical scores were reduced in the treatment group. Such results were found for all categories.

The invention claimed is:

1. A method for inhibiting cellular proliferation of fibroblasts-and/or glioma cells in a mammal comprising:
   administering a composition to a mammal wherein the composition includes an amount of a salt of a conjugate of dextran sulfate non-covalently linked to 2-(butane-1-sylfonylamino)-3-[4(4-piperidin-4-yl-butoxyl)-phenyl]-propionic acid effective to inhibit cellular proliferation of fibroblasts and/or gliomas in the mammal.

2. The method of claim 1 wherein the dextran sulfate has a sulfate content of greater than 2%.

3. The method according to claim 1, wherein the dextran sulfate has an average molecular weight in the range of 5,000 to 500,000 Daltons.

4. The method of claim 1 wherein the composition is administered post surgical procedure that results from an abdominal surgery, joint surgery, tendon surgery, surgery to remove pelvic sidewall adhesions, peritoneal surgery, thoracic surgery, vascular surgery, cardiac surgery, heart bypass surgery, heart valve replacement surgery, or open heart surgery, laminectomy, fallopian tube surgery, plastic surgery, arthritis & osteoarthritis, or surgery to treat temporo-mandibular joint dysfunction.

5. A method for inhibiting monocyte or macrophage invasion in a mammal, comprising:
   administering to a surgical site of the mammal where inhibition of monocyte or macrophage invasion is desired, an amount of a composition comprising a salt of a conjugate of dextran sulfate non-covalently linked to 2-(butane-1-sylfonylamino)-3-[4-(4-piperidin-4-yl-butoxyl)-phenyl]-propionic acid effective to inhibit monocyte or macrophage invasion and effective to prevent platelet activation at the site where inhibition of monocyte or macrophage invasion is desired.

6. The method of claim 5 wherein the dextran sulfate has a sulfate content of greater than 2%.

7. The method according to claim 5, wherein the dextran sulfate has an average molecular weight in the range of 5,000 to 500,000 Daltons.

8. The method of claim 5 wherein the composition is administered post surgical procedure that results from an abdominal surgery, joint surgery, tendon surgery, surgery to remove pelvic sidewall adhesions, peritoneal surgery, thoracic surgery, vascular surgery, cardiac surgery, heart bypass surgery, heart valve replacement surgery, or open heart surgery, laminectomy, fallopian tube surgery, plastic surgery, arthritis & osteoarthritis, or surgery to treat temporo-mandibular joint dysfunction.

9. A method for inhibiting neutrophil invasion comprising:
   administering to a site in a mammal where inhibition of neutrophil invasion is desired, an amount of a salt of a conjugate of dextran salt non-covalently liked to 2-(butane-1-sylfonylamino)-3-[4-(4-piperidin-4-yl-butoxyl)-phenyl]-propionic acid effective to inhibit neutrophil invasion and effective to prevent platelet activation at the site.

10. The method of claim 9 wherein the dextran sulfate has a sulfate content of greater than 2%.

11. The method according to claim 9, wherein the dextran sulfate has an average molecular weight in the range of 5,000 to 500,000 Daltons.

12. The method according to claim 1, wherein a secondary amine of 2-(butane-1-sylfonylamino)-3-[4-(4-piperidin-4-yl-butoxyl)-phenyl]-propionic acid is bonded to the C-1 carbon of the saccharide monomer at the reducing end of dextran sulfate.

13. The method according to claim 5, wherein a secondary amine of 2-(butane-1-sylfonylamino)-3-[4-(4-piperidin-4-yl-butoxyl)-phenyl]-propionic acid is bonded to the C-1 carbon of the saccharide monomer at the reducing end of dextran sulfate.

14. The method according to claim 9, wherein a secondary amine of 2-(butane-1-sylfonylamino)-3-[4-(4-(4-piperidin-4-yl-butoxyl)-phenyl]-propionic acid is bonded to the C-1 carbon of the saccharide monomer at the reducing end of dextran sulfate.

* * * * *